US011532400B2

(12) United States Patent
Thubagere Jagadeesh et al.

(10) Patent No.: US 11,532,400 B2
(45) Date of Patent: Dec. 20, 2022

(54) HYPERSPECTRAL SCANNING TO DETERMINE SKIN HEALTH

(71) Applicant: X Development LLC, Mountain View, CA (US)

(72) Inventors: Anupama Thubagere Jagadeesh, San Jose, CA (US); Brian Lance Hie, San Diego, CA (US)

(73) Assignee: X Development LLC, Mountain View, CA (US)

( * ) Notice: Subject to any disclaimer, the term of this patent is extended or adjusted under 35 U.S.C. 154(b) by 467 days.

(21) Appl. No.: 16/705,676

(22) Filed: Dec. 6, 2019

(65) Prior Publication Data

US 2021/0174965 A1 Jun. 10, 2021

(51) Int. Cl.
*G16H 50/00* (2018.01)
*G16H 50/30* (2018.01)
(Continued)

(52) U.S. Cl.
CPC .......... *G16H 50/30* (2018.01); *A61B 5/0071* (2013.01); *A61B 5/442* (2013.01); *A61B 5/443* (2013.01);
(Continued)

(58) Field of Classification Search
CPC ........ G16H 50/30; G16H 10/60; G16H 20/00; G16H 30/40; G16H 50/20; A61B 5/0071;
(Continued)

(56) References Cited

U.S. PATENT DOCUMENTS 5,999,840 A * 12/1999 Grimson ............... G16H 30/20
606/130
7,324,688 B2 1/2008 Rubinstenn et al.
(Continued)

FOREIGN PATENT DOCUMENTS

CN 106983493 A * 7/2017 ........... A61B 5/0077
EP 1297782 4/2003

OTHER PUBLICATIONS

Jedynak et al., Statistical Models for Skin Detection, 2003 Conference on Computer Vision and Pattern Recognition Workshop (vol. 8, pp. 92) (Year: 2003).*

*Primary Examiner* — Nancy Bitar
*Assistant Examiner* — Xiao Liu
(74) *Attorney, Agent, or Firm* — Fish & Richardson P.C.

(57) ABSTRACT

A system, method, and computer readable media are provided for obtaining a first set of skin data from an image capture system including at least one ultraviolet (UV) image of a user's skin. Performing a correction on the skin data using a second set of skin data associated with the user. Quantifying a plurality of skin parameters of the user's skin based on the first skin data, including quantifying a bacterial load. Quantifying the bacterial load by applying a brightness filter to isolate portions of the at least one UV image containing fluorescence, applying a dust filter, identifying portions of the at least one UV image that contain fluorescence due to bacteria, and determining a quantity of bacterial load in the users skin. Determining, using a machine learning model, an output associated with a normal skin state of the user and a current skin state of the user.

18 Claims, 5 Drawing Sheets

(51) Int. Cl.

| | | |
|---|---|---|
| *G06Q 30/06* | (2012.01) | |
| *G16H 10/60* | (2018.01) | |
| *G06N 3/08* | (2006.01) | |
| *G06N 3/04* | (2006.01) | |
| *G06T 7/44* | (2017.01) | |
| *G06T 5/40* | (2006.01) | |
| *G06T 7/00* | (2017.01) | |
| *G06T 5/50* | (2006.01) | |
| *G06T 7/11* | (2017.01) | |
| *G06T 7/90* | (2017.01) | |
| *A61B 5/00* | (2006.01) | |
| *G16H 20/00* | (2018.01) | |

(52) U.S. Cl.
CPC .............. *A61B 5/445* (2013.01); *A61B 5/486* (2013.01); *A61B 5/7267* (2013.01); *G06N 3/04* (2013.01); *G06N 3/08* (2013.01); *G06Q 30/0631* (2013.01); *G06T 5/40* (2013.01); *G06T 5/50* (2013.01); *G06T 7/0016* (2013.01); *G06T 7/11* (2017.01); *G06T 7/44* (2017.01); *G06T 7/90* (2017.01); *G16H 10/60* (2018.01); *G16H 20/00* (2018.01); *A61B 2576/02* (2013.01); *G06N 3/0445* (2013.01); *G06T 2207/10064* (2013.01); *G06T 2207/20084* (2013.01); *G06T 2207/30088* (2013.01)

(58) Field of Classification Search
CPC ......... A61B 5/442; A61B 5/443; A61B 5/445; A61B 5/486; A61B 5/7267; A61B 2576/02; G06N 3/04; G06N 3/08; G06N 3/0445; G06N 3/0454; G06N 7/005; G06Q 30/0631; G06T 5/40; G06T 5/50; G06T 7/0016; G06T 7/11; G06T 7/44; G06T 7/90; G06T 2207/10064; G06T 2207/20084; G06T 2207/30088; G06T 2207/20081

See application file for complete search history.

(56) References Cited

U.S. PATENT DOCUMENTS

| | | | |
|---|---|---|---|
| 7,437,344 B2 | 10/2008 | Peyrelevade | |
| 7,894,651 B2 | 2/2011 | Gutkowicz-Krusin et al. | |
| 9,525,867 B2 | 12/2016 | Thomas et al. | |
| 2009/0245603 A1* | 10/2009 | Koruga | G06T 7/0012 382/128 |
| 2009/0253162 A1* | 10/2009 | Windsor | G01N 33/52 435/29 |
| 2010/0185064 A1 | 7/2010 | Bandic et al. | |
| 2010/0328740 A1* | 12/2010 | Tsukada | H04N 1/6086 358/530 |
| 2013/0300850 A1* | 11/2013 | Millikan | H04N 5/332 348/77 |
| 2017/0154238 A1* | 6/2017 | Li | G06V 10/56 |

* cited by examiner

HYPERSPECTRAL SCANNING TO DETERMINE SKIN HEALTH

TECHNICAL FIELD

This disclosure generally relates to quantifying skin health. More particularly the disclosure relates to processes for using machine learning algorithms to quantify parameters associated with a user's skin.

BACKGROUND

Skin health of an individual is dependent on many separate, time changing factors. In order to ensure an individual is able to maintain their skin in the best of health, a technique to readily measure and predict future skin conditions of an individual is desirable.

SUMMARY

This specification describes systems, methods, devices, and other techniques for performing skin health assessments using machine learning analysis of data captured at an image capture system. The system can process optical images of a user's skin and quantify health parameters associated with the images. For example, a machine learning system is used to recognize patterns of variations of a user's skin over time. The system can use the recognized patterns to determine various parameters associated with a user's skin. The system can provide an output to the user that gives insights on the health of the user's skin. The present system for processing optical images of a user's skin can quantify the bacterial load on a user's skin, the pigmentations and redness, skin roughness, and collagen content, or any suitable combination thereof.

In general, innovative aspects of the subject matter described in this specification can be embodied in methods that include the actions of obtaining a first set of skin data from an image capture system including at least one ultraviolet (UV) image of a user's skin. Performing a correction on the skin data using a second set of skin data associated with the user. The second set of skin data having been collected prior to obtaining the first set of skin data, and having been stored in a repository. Quantifying a plurality of skin parameters of the user's skin based on the first skin data, including quantifying a bacterial load. Quantifying the bacterial load by applying a brightness filter to isolate portions of the at least one UV image containing fluorescence, applying a dust filter using an expectation maximization algorithm and a two-component Gaussian mixture model to eliminate portions of the image that contain fluorescence caused by dust particles, using a loopy belief propagation algorithm to identify portions of the at least one UV image that contain fluorescence due to bacteria, and determine a quantity of bacterial load in the users skin. Determining, by providing the plurality of quantified skin parameters as input to a machine learning model, an output associated with a normal skin state of the user and a current skin state of the user based on the plurality of quantified skin parameters and providing data indicating the output for display on a user computing device.

These and other implementations can each optionally include one or more of the following features.

In some implementations, the second skin data associated with the user and collected prior to the first skin data is collected on multiple occasions. In some implementations at routine intervals (e.g., daily, weekly, or monthly).

In some implementations, the first and second skin data includes at least three sets of three images, with three natural images taken in white light, three polarized images taken in polarized light, and three UV images taken in UV light, each set of three images taken from a different angle.

In some implementations, the plurality of skin parameters quantified includes skin pigmentation, redness, and skill roughness/collagen content, or any suitable combination thereof.

In some implementations, the correction performed using the second skin data is a color correction that includes applying a first adjustment to the first skin data based on a reference color present in the second skin data, applying a second adjustment to the first skin data using a histogram matching algorithm, and applying a third adjustment to the first skin data by performing a lighting correction.

In some implementations, the first skin data is segmented into a plurality of portions based on determining anatomy features present in the first skin data and the plurality of parameters are quantified separately for each portion of the user's skin.

In some implementations, external data associated with the user can be obtained and provided as additional input to the machine learning model.

In some implementations, providing the data indicating the output includes providing data indicating a skin care product recommendation to improve a health of the user's skin.

The details of one or more implementations of the subject matter of this disclosure are set forth in the accompanying drawings and the description below. Other features, aspects, and advantages of the subject matter will become apparent from the description, the drawings, and the claims.

DESCRIPTION OF DRAWINGS

Like reference numbers and designations in the various drawings indicate like elements.

DETAILED DESCRIPTION

This disclosure describes methods and systems for processing optical images of a user's skin and quantifying health parameters associated with the images. For example, a machine learning system is used to recognize patterns of variations of a user's skin over time. The system can use the recognized patterns to determine various parameters associated with a user's skin. The system can provide an output to the user that gives insights on the health of the user's skin. The present system for processing optical images of a user's skin can quantify the bacterial load on a user's skin, the pigmentations and redness, skin roughness, and collagen content, or any suitable combination thereof.

Figure 1:
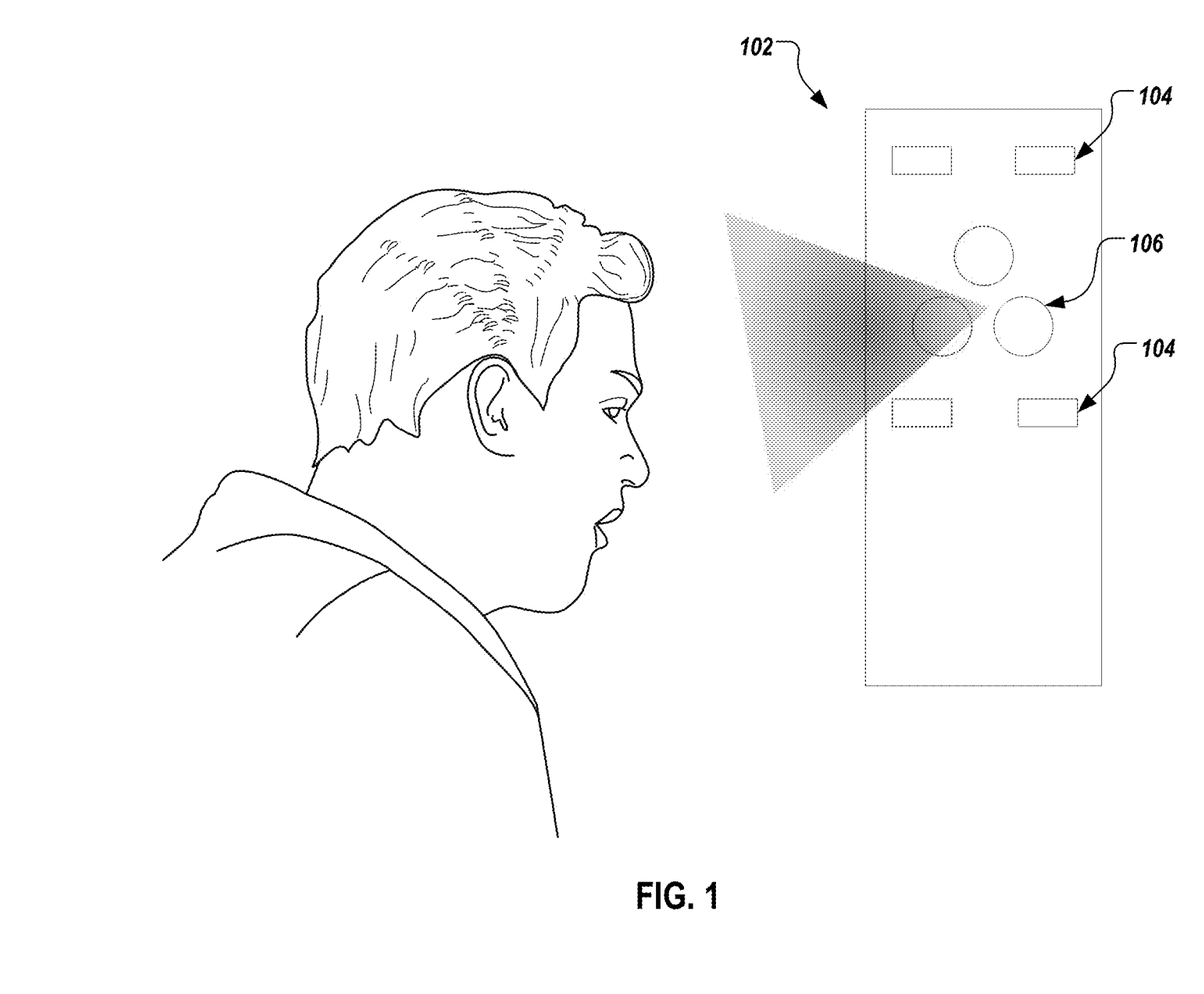
FIG. 1 depicts a system for capturing skin data associated with an individual.

FIG. 1 depicts a system for capturing skin data associated with an individual. The image capture system 102 includes a camera and lighting system configured to capture optical images of a user's skin. The image capture system 102 includes illuminators 104 and one or more sensors 106. The illuminators 104 form the lighting system and provide electromagnetic radiation (light) at specific wavelengths. In some examples, the illuminators 104 provide light at predetermined wavelengths that improve the quality of skin data recorded by the image capture system 102. For example, the illuminators 104 can be configured (e.g., through the use of filters and/or activation of particular light sources) to emit light at wavelengths that aid in the detection of particular skin conditions. The illuminators 104 can be, for example, light emitting diodes (LEDs) or halogen lights, or a combination thereof. The illuminators 104 can provide multiple specific types of light. For example, white light, or regular fluorescent light. In another example the illuminators 104 can emit polarized light, with a majority of the emitted electromagnetic radiation having aligned electric fields (e.g. parallel, cross or circular polarized light). In yet another example the illuminators 104 can emit ultraviolet (UV) light, for example, at a wavelength of 400 nm or less. The image capture system 102 can have multiple illuminators, which can emit any suitable combination of the above types of light.

The image capture system 102 includes one or more sensors 106. The sensors 106 can be image sensors, configured to receive light that is emitted from the illuminators 104 and reflected off a user's skin. The image sensors 106 can receive light at specific wavelengths, such as near-IR (NIR), visible, and ultra violet (UV) light or any combination thereof. For example, the sensors 106 can detect light between 300 nm and 1000 nm wavelengths. In some examples, the image sensors can be wavelength controlled. For example, wavelength controlled image sensors are able to detect specific light polarizations (e.g. parallel, cross or circular polarized light). The image sensors are capable of collecting a hyperspectral scan using standard photography, fluorescent photography, polarized photography and video. The image sensors can be, but are not limited to, cameras that includes charge-coupled device (CCD) or a complementary metal oxide-semiconductor (CMOS) sensor.

Figure 2:
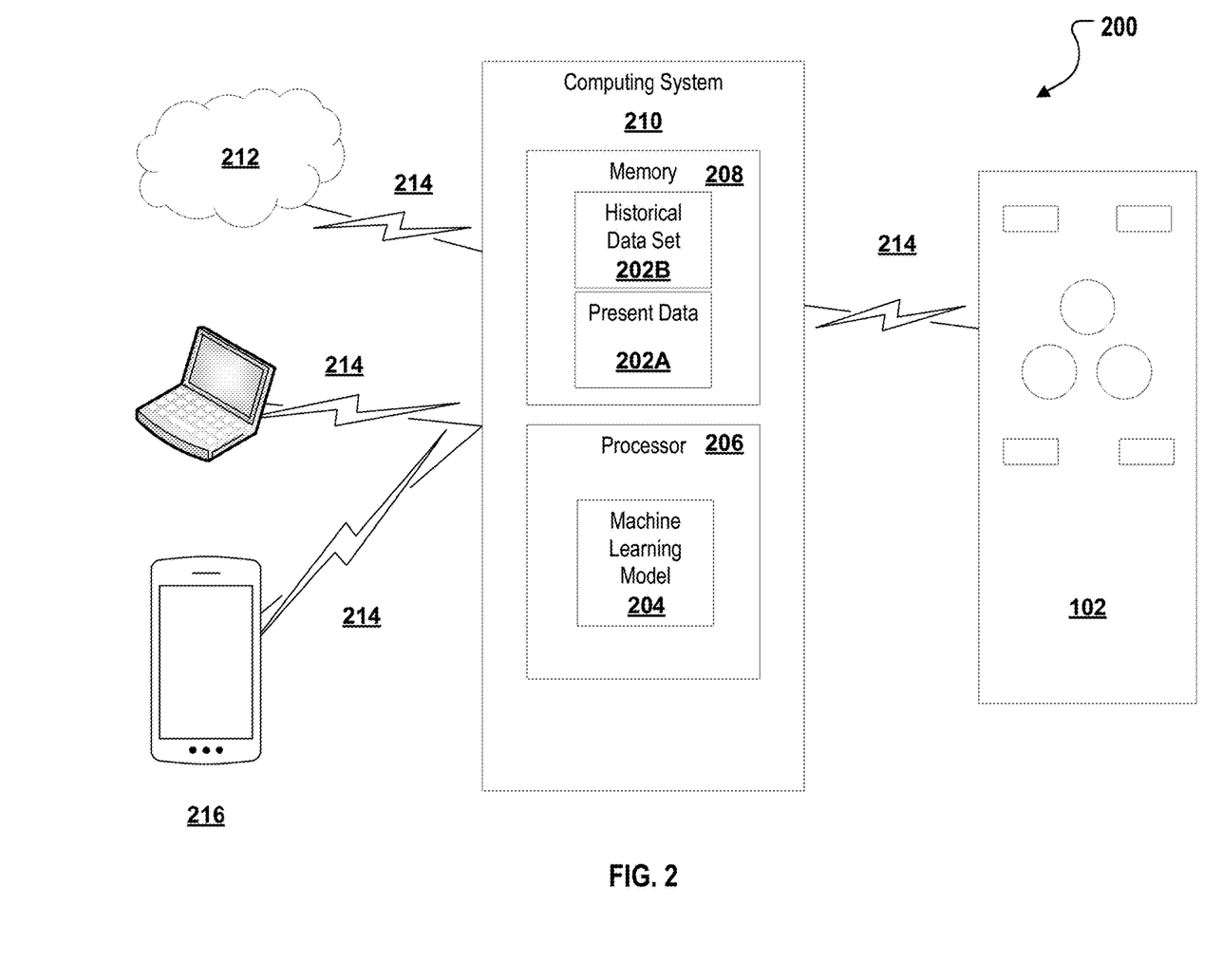
FIG. 2 depicts a block diagram of a system for capturing skin data.

FIG. 2 depicts a block diagram of a system for capturing skin data 200. It includes the image capture system 102 as described in FIG. 1, as well as a computing system 210. The computing system 210 and the image capture system 102 can communicate via a communications link 214. The communication link 214 provides communications for the image capture system 102 with the computing system 210. The communication interface 214 can be but is not limited to a wired communication interface (e.g., USB, Ethernet, fiber optic) or wireless communication interface (e.g., Bluetooth, ZigBee, WiFi, infrared (IR), CDMA2000, etc.). The communication interface 214 can be used to communicate directly or indirectly, e.g., through a network, with the computing system 210.

The computing system 210 receives present skin data 202A from the image capture system 102 via the communications link 214. Present skin data 202A can be data included in the most recent images taken of the user's skin. The computing system 210 can also receive present skin data 202A from other user devices 216, or a network 212. In some implementations the present skin data can be received in real-time. The present skin data 202A is then used by the machine learning model 204 to generate a quantified output. The present skin data 202A can include one of, or any combination of several images at different angles and under different illumination conditions. For example, in one implementation the present skin data includes at least 9 images, in three sets of three. In this implementation there can be an image taken in white light, an image taken in polarized light, and an image taken in UV light for each of three different angles (for example, a frontal image, a side image, and an elevated image). In another implementation there may be more or less images in the present skin data 202A. The present skin data 202A can also include medical information and environmental factors.

Medical information can include, but is not limited to, a user's age, activity levels, diet, current or past medications, or any combination thereof. The user may volunteer this information, for example, during an account registration step, or when prompted by the computing system 210 via a communications interface 214.

Environmental factors can include, but are not limited to, the temperature, relative humidity, pollen count, UV index, or any combination thereof. Environmental factors may be obtained via a known user's location, or by additional sensors on the image capture system 102, or any combination thereof.

The computing system 210 can store in memory a historical data set 202B for a user. The historical data set can include all data that has previously been used, or a subset of the previous data. The historical data set 202B can also include data relating to common trends seen across multiple individuals, or trends seen among particular demographics such as race, age group, sex, or any suitable combination thereof.

The machine learning model 204 receives the present skin data 202A, and the historical data 202B and generates a quantified output. For example, the machine learning model 204 can compare the present skin data (e.g., present hyperspectral scan images of the user's skin) with historical data (e.g., historical hyperspectral scan images of the user's skin) to identify changes in the user's skin health over a period of time. For example, the machine learning model 204 can identify, and in some implementations locate, minute changes in the regions of the user's skin, such as changes of moisture content, changes in coloration, bacterial load, hyperpigmentation, blood flow, or a combination thereof. The machine learning model 204 can correlate the detected changes in the user's skin with known patterns of skin health (e.g., a library of skin symptoms that lead to various skin conditions) to generate a predictive output of the user's future skin health. The predictive output can include, but is not limited to a type of future skin condition that the user is likely to experience, a location of a predicted skin condition, or a combination thereof.

In some implementations, the machine learning model 204 is a deep learning model that employs multiple layers of models to generate an output for a received input. A deep neural network is a deep machine learning model that includes an output layer and one or more hidden layers that each apply a non-linear transformation to a received input to generate an output. In some cases, the neural network may be a recurrent neural network. A recurrent neural network is a neural network that receives an input sequence and generates an output sequence from the input sequence. In particular, a recurrent neural network uses some or all of the internal state of the network after processing a previous input in the input sequence to generate an output from the current input in the input sequence. In some other implementations, the machine learning model 204 is a convolutional neural network. In some implementations, the machine learning model 204 is an ensemble of models that may include all or a subset of the architectures described above.

In some implementations, the machine learning model 204 can be a feedforward auto-encoder neural network. For example, the machine learning model 204 can be a three-layer auto-encoder neural network. The machine learning model 204 may include an input layer, a hidden layer, and an output layer. In some implementations, the neural network has no recurrent connections between layers. Each layer of the neural network may be fully connected to the next, e.g., there may be no pruning between the layers. The neural network may include an optimizer for training the network and computing updated layer weights, such as, but not limited to, ADAM, Adagrad, Adadelta, RMSprop, Stochastic Gradient Descent (SGD), or SGD with momentum. In some implementations, the neural network may apply a mathematical transformation, e.g., a convolutional transformation or factor analysis to input data prior to feeding the input data to the network.

In some implementations, the machine learning model 204 can be a supervised model. For example, for each input provided to the model during training, the machine learning model 204 can be instructed as to what the correct output should be. The machine learning model 204 can use batch training, e.g., training on a subset of examples before each adjustment, instead of the entire available set of examples. This may improve the efficiency of training the model and may improve the generalizability of the model. The machine learning model 204 may use folded cross-validation. For example, some fraction (the "fold") of the data available for training can be left out of training and used in a later testing phase to confirm how well the model generalizes. In some implementations, the machine learning model 204 may be an unsupervised model. For example, the model may adjust itself based on mathematical distances between examples rather than based on feedback on its performance.

A machine learning model 204 can be trained to recognize patterns in skin condition when compared with the historical data of an individual, and environmental parameters. In some examples, the machine learning model 204 can be trained on hundreds of hyperspectral scans of an individual's skin. The machine learning model 204 can be trained to identify potential breakouts and signs of future skin care needs.

The machine learning model 204 can be, for example, a deep-learning neural network or a "very" deep learning neural network. For example, the machine learning model 204 can be a convolutional neural network. The machine learning model 204 can be a recurrent network. The machine learning model 204 can have residual connections or dense connections. The machine learning model 204 can be an ensemble of all or a subset of these architectures. The machine learning model 204 is trained to quantify several parameters of a user's skin based on detecting patterns from one or more of the present skin data 202A and the historical data set 202B. The model may be trained in a supervised or unsupervised manner. In some examples, the model may be trained in an adversarial manner. In some examples, the model may be trained using multiple objectives, loss functions or tasks.

The machine learning model 204 can be configured to provide a binary output, e.g., a yes or no indication of whether the user's skin is in a healthy condition. In some examples, the machine learning model 204 is configured to determine a type of skin condition of the user. Types of skin conditions that can be detected include, but are not limited to, acne, wrinkles, pores, discolorations, hyperpigmentation, spots, blackheads, whiteheads, dry patches, moles, and psoriasis. In some implementations, the output data of the machine learning model 204 can be used for orthogonal diagnosis of women's health (e.g., ovulation).

In some implementations, the machine learning model 204 can provide suggested treatment options for the user to treat the predicted skin condition. For example, the computing system 210 can send the quantified output data to the user's dermatologist. Specifically, the computing system 210 can send the predictive output data to a computing device registered to the user's dermatologist. In some implementations, the computing system 210 can provide recommendations for a skincare product that treats or helps to prevent the predicted skin condition. Specifically, the computing system 210 can send the recommendations to a computing device 216 associated with the user.

Further to the descriptions above, a user may be provided with controls allowing the user to make an election as to both if and when systems, programs, or features described herein may enable collection of user information. In addition, certain data may be treated in one or more ways before it is stored or used, so that personally identifiable information is removed. For example, a user's identity may be treated so that no personally identifiable information can be determined for the user, or a user's test data and/or diagnosis cannot be identified as being associated with the user. Thus, the user may have control over what information is collected about the user and how that information is used.

Figure 3:
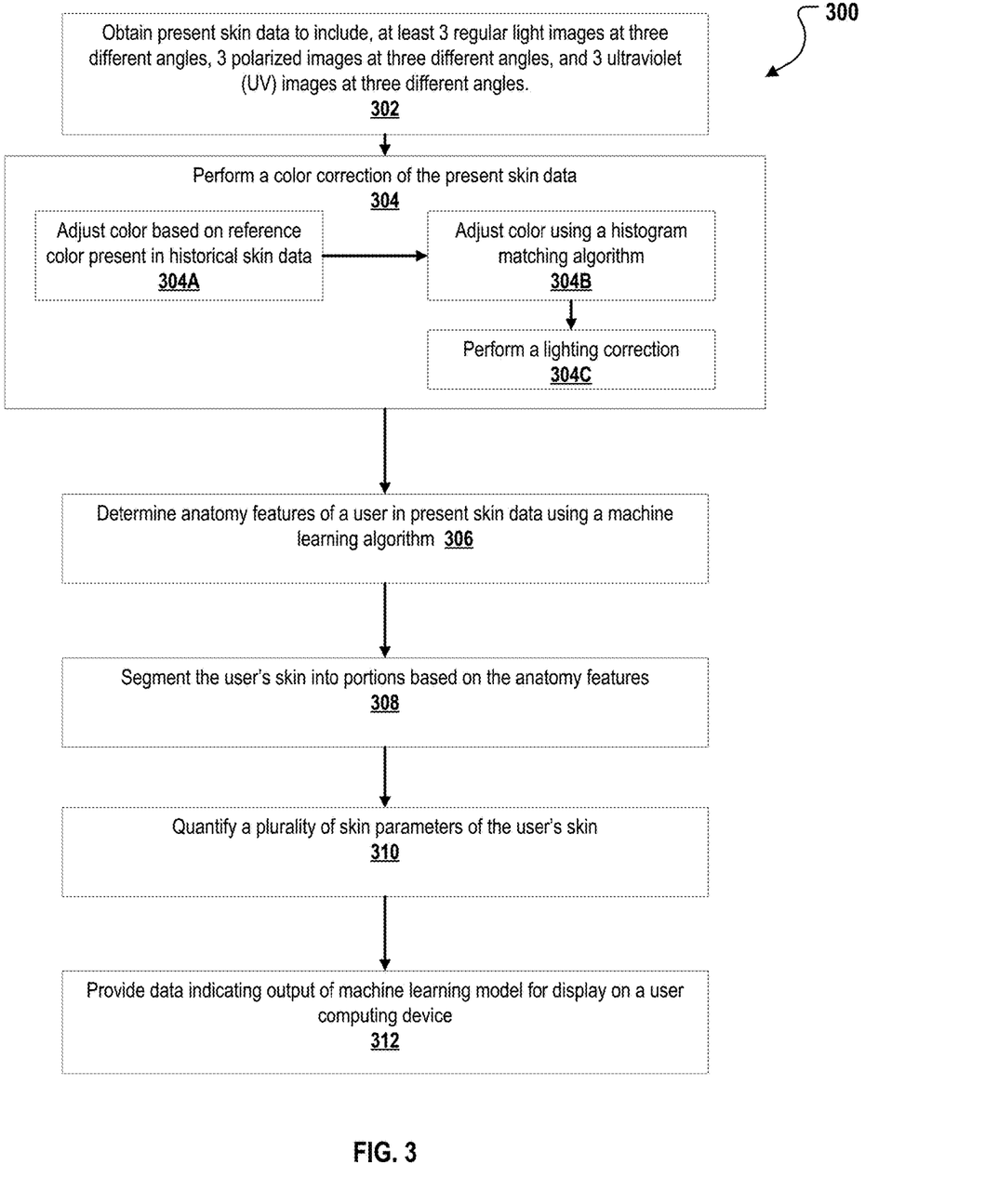
FIG. 3 depicts a flowchart of an example process for processing skin data.

FIG. 3 is a flow diagram of a method 300 for determining a user's skin health in one example implementation. However, it will be understood that method 300 may be performed, for example, by any suitable system, environment, software, and hardware, or a combination of systems, environments, software, and hardware as appropriate. In some instances, method 300 can be performed by system for capturing skin data 200, or portions thereof, described in FIG. 2, as well as other components or functionality described in other portions of this description. In other instances, method 300 may be performed by a plurality of connected components or systems. Any suitable system(s), architecture(s), or application(s) can be used to perform the illustrated operations.

The system obtains present skin data (302). The present skin data can be collected from a system similar to the image capture system 102 as described in FIG. 1. In some implementations, the present skin data can include at least three high definition images taken from three different angles under regular (non-polarized, substantially white light) illumination, three images taken from three different angles under polarized illumination, and three images taken from three different angles under UV illumination. Regular illumination from a point light source can provide textural and contour information (for example, the depth of wrinkles on the skin). Textural and contour information can be, for example, inferred by the amount of shadow versus illumination induced by the light source. Polarized light can provide a diffuse light source with more consistent illumination than what is typically provided by a single point light source. Polarized light can be used, for example, to improve comparison between different regions of the skin (for example, changes in pigmentation across the face) without necessarily requiring controls or corrections for variable levels of illumination. UV illumination can be used to measure the amount of UV reflectivity of skin. For example, less reflective regions of a user's skin can indicate higher amounts of sun damage and UV-related skin burn. UV illumination can also cause bacterial proteins to fluoresce, allowing for quantification of bacterial load on the skin.

For example, the image capture system can record images of an area of a user's skin positioned in front of the system. In some examples, the image capture system records multiple sets of images. For example, the image capture system can record three sets of three images. Each set of images can include an image taken from a front angle, and image taken from a left angle, and an image taken from a right angle. In another implementation the three angles can be front, side and top, or any suitable combination of angles. The present skin data can be stored in a repository for later use as historical skin data, as well as for to be further processed in method 300. In another example, the image capture system can record only one set of three images, three UV images, or any other suitable combination of images.

At 304, a color correction of the present skin data is performed. In some implementation the color correction is provided using three distinct steps. At 304A, an initial correction is applied based on one or more reference colors selected from one or more historical skin data sets. For example, if it is determined that a user's iris are present in the skin data, and that iris rarely change color, the color of the user's iris can be used as a reference to apply a color correction. Similarly the whites of the user's eyes can be used as another reference color. In some implementations a fiducial marker, such as a high contrast black and white image, can be present in the background, or near the skin in some or all of the historical skin data. The fiducial marker can be used to provide one or more additional reference colors. At 304B, a histogram matching algorithm is used to further adjust image color. The histogram matching algorithm can measure a red/green/blue (RGB) histogram of a reference image (for example from a historical data set, or an average of the historical data), and then adjust the present data set's colors to achieve a matching, or nearly matching RGB histogram. Finally at 304C a lighting correction is performed, adjusting the image based on the known illuminators active at the time. For example, for a known lighting source, or a lighting source that can be computationally inferred from the image, then the lighting values can be corrected to remove differentially illuminated regions of skin.

At 306, the anatomy features in the present skin data are determined. In some implementations, the anatomy features are determined using a machine learning algorithm. Anatomy features may include, but are not limited to, a nose, eyes, chin, cheeks, mouth, eyebrows, ears, fingers, knuckles, joints, or any combination thereof. Based on the identified anatomy features, regions of the present skin data can be determined.

At 308, the present skin data is broken into segments based on the anatomy features. For example, the system can segment skin data by identifying landmark features in one or more of the images of the skin. In some examples each image is segmented. For example, a user's face may include 68 landmark features (e.g., eyebrow, edge of lips, etc.) that are identified. A point associated with a location of the landmark can be associated with the present skin data, and triangles can be drawn between groups of three points. Each triangle can be a segment of skin and can be uniquely associated with a particular region (e.g., an upper cheek, a left jawline, a forehead region, etc.).

At 310, a plurality of skin parameters can be quantified for the user's skin. In some implementations the parameters can be quantified for each segment of skin, or a subset of the parameters can be quantified for all segments, while a different subset is only quantified for certain segments. The parameters to be quantified can include, but are not limited to, bacterial load, skin pigmentation, redness, skin roughness, collagen content, moisture content, changes in coloration, blood flow, or any suitable combination thereof. The quantification of skin parameters is discussed in further detail below with reference to FIG. 4.

At 312, data indicating the output of the machine learning model is provided for display on a user computing device. The user computing device can be any suitable device, such as a smart phone, tablet, PC, or PDA. In some instances the user computing device may be a device associated with a user's dermatologist. In other instances the data is provided directly to the user, or to a combination of people authorized to view the data.

Figure 4:
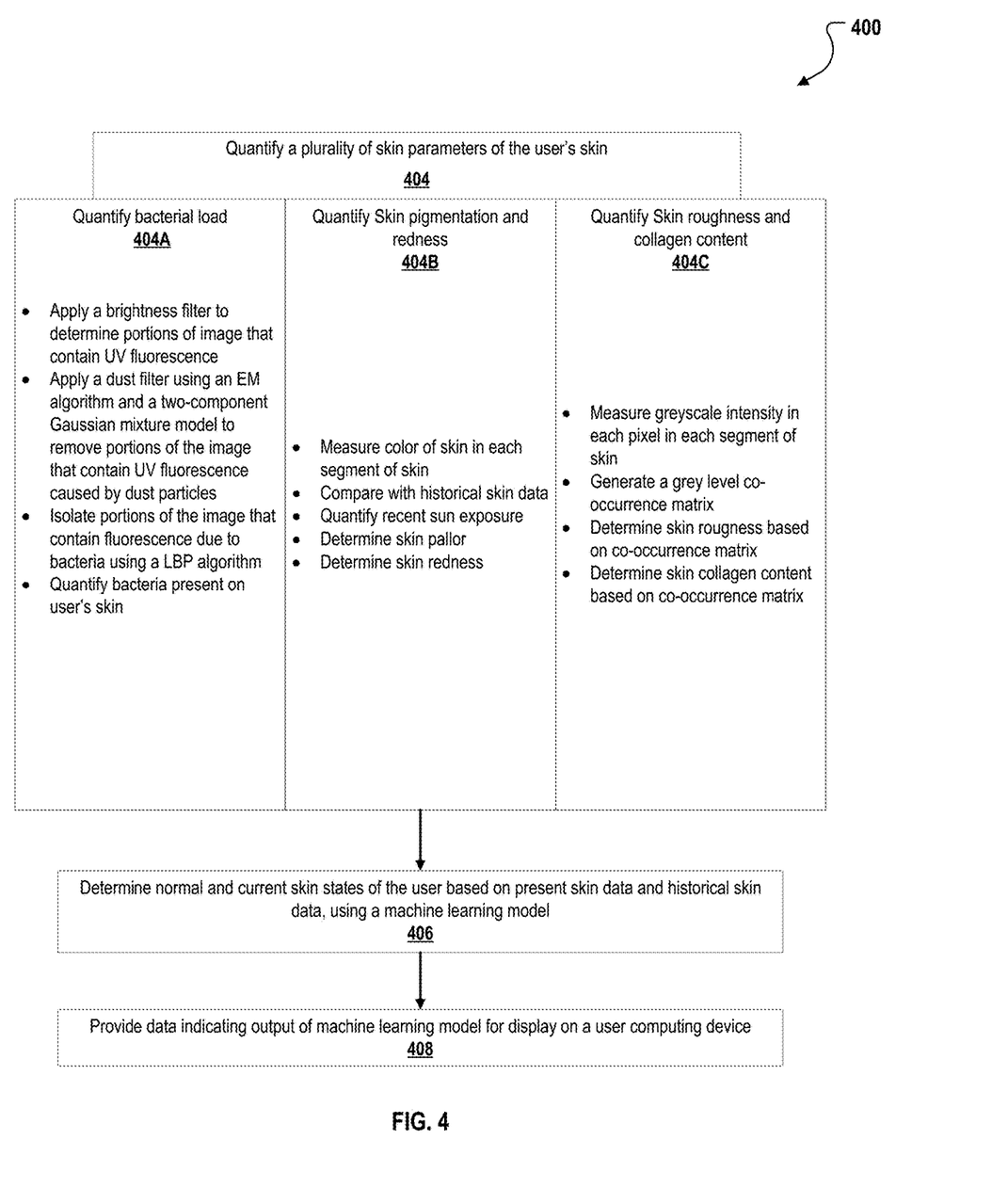
FIG. 4 depicts a flowchart of an example process for quantifying skin parameters.

FIG. 4 is a flowchart depicting a method 400 for quantifying skin parameters of a user's skin in one example implementation. However, it will be understood that method 400 may be performed, for example, by any suitable system, environment, software, and hardware, or a combination of systems, environments, software, and hardware as appropriate. In some instances, method 400 can be performed by system for capturing skin data 200, or portions thereof, described in FIG. 2, as well as other components or functionality described in other portions of this description. In other instances, method 400 may be performed by a plurality of connected components or systems. Any suitable system (s), architecture(s), or application(s) can be used to perform the illustrated operations.

At 404, skin parameters identified in the present skin data are quantified. The quantified parameters can be, but are not limited to bacterial load, skin pigmentation, redness, skin roughness, collagen content, moisture content, changes in coloration, or blood flow. In some implementations three separate processes are used to quantify skin parameters, as described in 404A, 404B, and 404C. These three processes can occur simultaneously, or at different times. 404A, 404B, and 404C can be performed by the same system, for example the computing system 210 as described in FIG. 2, or by separate systems.

At 404A, bacterial load is quantified. For example, bacterial load can be quantified by segmenting regions of the image that contain fluorescent bacteria from regions that do not. Bacterial load segmentation can be implemented through various algorithms, the following example is described herein in further detail. Initially a brightness filter can be applied to one or more UV images in the present skin data to determine any portions of or pixels in an image that contain UV fluorescence. Once portions of the skin data that contain fluorescence are identified, a dust filter can be applied to remove fluorescence that is consistent with the reflectivity of fluorescent dust, rather than bacteria on the user's skin. The dust filter can be based on a manually tuned color value cutoff or can be a machine learning algorithm such as an expectation-maximization (EM) algorithm. The EM algorithm can lean separate probability distributions (for example, a mixture of Gaussian distributions) where one or more distributions describe the portions of the image containing dust while other distributions describe other portions of the image. The algorithm with these learned distributions can determine if fluorescence is due to dust particles, or bacteria, and remove fluorescence that is determined to be due to dust. The remaining portions of the present skin data that contain fluorescence can then be isolated and de-noised using a Loopy Belief Propagation (LBP) algorithm. The LBP algorithm is an extension of the Belief Propagation algorithm that does approximate inference on general probabilistic graphical models (PGMs) (for example, an image in which pixels are represented as nodes in a PGM and where edges connect adjacent pixels). The LBP algorithm isolates and segments portions of the images that contain fluorescence, assigning a higher likelihood of a portion containing fluorescence if that portion is adjacent to another portion that has already been determined to contain fluorescence and if that portion has color values that are more consistent with bacterial fluorescence. Once the portions of the present skin data that contain bacterial fluorescence are determined, an overall bacterial load can be quantified for the present skin data. In some implementation other parameters can be quantified indirectly using the bacterial load measurement. For example, skin hydration and skin pH can be inferred from the bacterial load data collected.

At 404B the skin pigmentation and redness of the user are quantified. Skin color can be quantified for each individual segment of the user's skin. In some implementations, the color can then be compared on a segment by segment basis with historical skin data. In some implementations the skin color can be measured as an average color across an entire segment, and quantified as a Euclidean distance from true white. In other implementations the skin color can be quantified for individual portions of the segment (e.g., individual pixels). The quantified skin color can then be compared with historical skin data to determine a change in skin color or pigmentation. In some implementations local weather data can be used to identify a correlation between a change in skin pigmentation and weather. For example, if it has been relatively cloudy in a time interval between the most recent historical data and the present data, the user's skin may be paler, or have less pigmentation than previously. This may be explained in part, by the weather. Local weather data may be provided by the user, or automatically retrieved based on a user's location information. In some implementations the change in skin pigmentation can be used to extrapolate other health conditions, for example, sunburn, or as an early indicated of jaundice.

At 404C, skin roughness and collagen content is quantified. Each portion of each segment of the present skin data can be given an intensity rating. In some implementations an intensity level co-occurrence matrix can then be generated from the present skin data and skin roughness can be determined based on the co-occurrence matrix. In some implementations skin roughness and the co-occurrence matrix can be compared to a corpus of data containing skin roughness measurements and co-occurrence matrices associated with a multitude of other users, as well as historical data for the current user. In some implementations a collagen content can be determined based on the determined skin roughness, as well as the historical skin data of the user.

At 406, the quantified skin parameters are compared with historical skin data, and a current skin state and a normal skin state are determined by a machine learning model. The machine learning model can be similar to machine learning model 204 as described with reference to FIG. 2. Skin state can include, but is not limited to, acne detection, identification of moles, freckles, melanoma, or keratosis, skin hydration, skin pH, sunburn, irritation, or any suitable combination thereof. In some implementations the machine learning model can also receive external data inputs, such as date and time from timestamps associated with the images, a personal log, environmental conditions, a user's diet, location, HF ultrasound data, near IR information, or any suitable combination.

At 408, data indicating the output of the machine learning model is provided for display on a user computing device. The user computing device can be any suitable device, such as a smart phone, tablet, PC, or PDA. In some instances the user computing device may be a device associated with a user's dermatologist. In other instances the data is provided directly to the user, or to a combination of people authorized to view the data.

Figure 5:
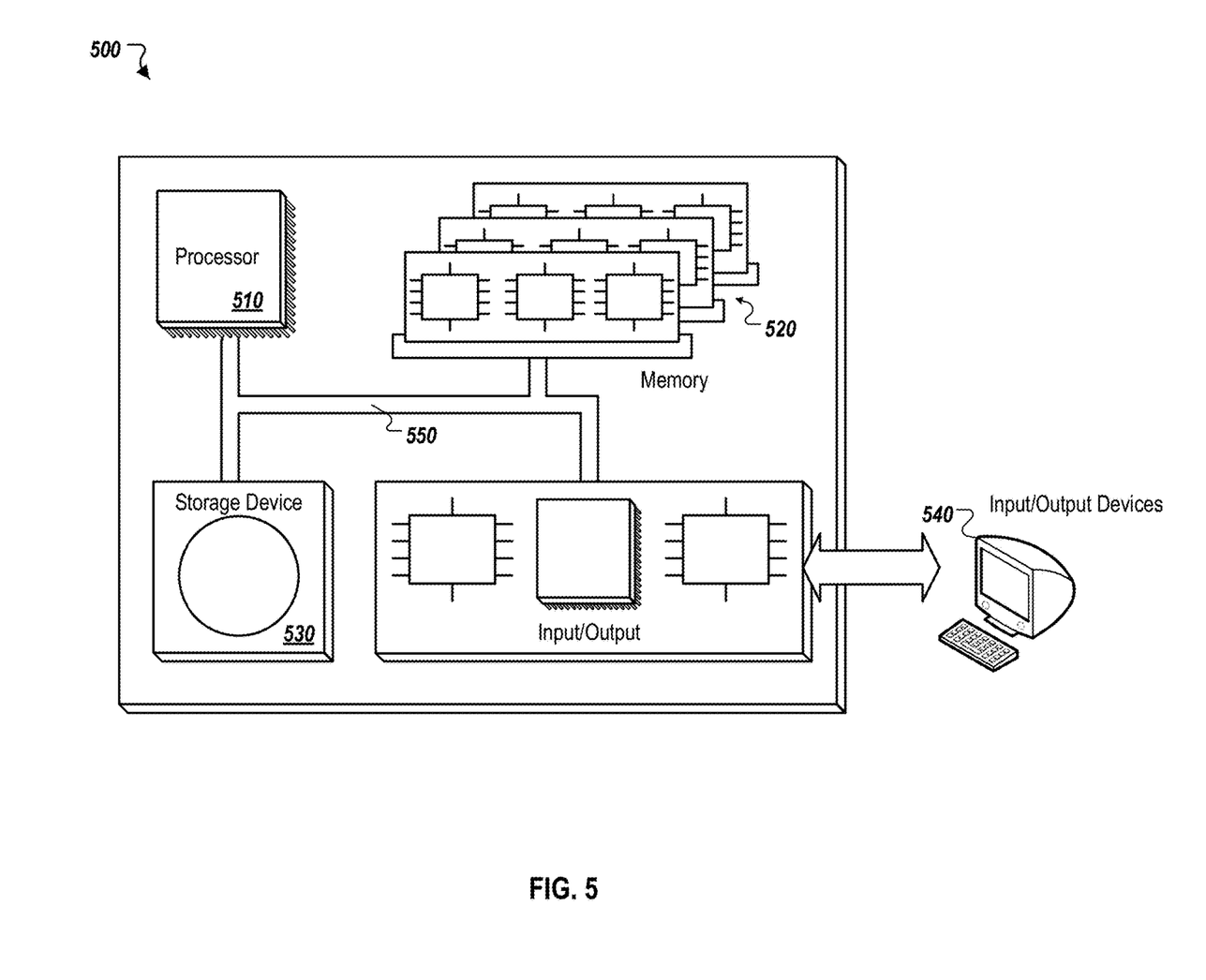
FIG. 5 depicts a schematic diagram of a computer system that may be applied to any of the computer-implemented methods and other techniques described herein.

FIG. 5 is a schematic diagram of a computer system 500. The system 500 can be used to carry out the operations described in association with any of the computer-implemented methods described previously, according to some implementations. In some implementations, computing systems and devices and the functional operations described in this specification can be implemented in digital electronic circuitry, in tangibly-embodied computer software or firmware, in computer hardware, including the structures disclosed in this specification (e.g., system 500) and their structural equivalents, or in combinations of one or more of them. The system 500 is intended to include various forms of digital computers, such as laptops, desktops, workstations, personal digital assistants, servers, blade servers, mainframes, and other appropriate computers, including vehicles installed on base units or pod units of modular vehicles. The system 500 can also include mobile devices, such as personal digital assistants, cellular telephones, smartphones, and similar computing devices. Additionally, the system can include portable storage media, such as, Universal Serial Bus (USB) flash drives. For example, the USB flash drives may store operating systems and other applications. The USB flash drives can include input/output components, such as a wireless transducer or USB connector that may be inserted into a USB port of another computing device.

The system 500 includes a processor 510, a memory 520, a storage device 530, and an input/output device 540. Each of the components 510, 520, 530, and 540 are interconnected using a system bus 550. The processor 510 is capable of processing instructions for execution within the system 500. The processor may be designed using any of a number of architectures. For example, the processor 510 may be a CISC (Complex Instruction Set Computers) processor, a RISC (Reduced Instruction Set Computer) processor, or a MISC (Minimal Instruction Set Computer) processor.

In one implementation, the processor 510 is a single-threaded processor. In another implementation, the processor 510 is a multi-threaded processor. The processor 510 is capable of processing instructions stored in the memory 520 or on the storage device 530 to display graphical information for a user interface on the input/output device 540.

The memory 520 stores information within the system 500. In one implementation, the memory 520 is a computer-readable medium. In one implementation, the memory 520 is a volatile memory unit. In another implementation, the memory 520 is a non-volatile memory unit.

The storage device 530 is capable of providing mass storage for the system 500. In one implementation, the storage device 530 is a computer-readable medium. In various different implementations, the storage device 530 may be a floppy disk device, a hard disk device, an optical disk device, or a tape device.

The input/output device 540 provides input/output operations for the system 500. In one implementation, the input/output device 540 includes a keyboard and/or pointing device. In another implementation, the input/output device 540 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Further to the descriptions above, a user may be provided with controls allowing the user to make an election as to both if and when systems, programs, or features described herein may enable collection of user information. In addition, certain data may be treated in one or more ways before it is stored or used, so that personally identifiable information is removed. For example, a user's identity may be treated so that no personally identifiable information can be determined for the user, or a user's skin data and/or diagnosis cannot be identified as being associated with the user. Thus, the user may have control over what information is collected about the user and how that information is used Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A system for assessing skin health, comprising:
one or more processors;
one or more tangible, non-transitory media operably connectable to the one or more processors and storing instructions that, when executed, cause the one or more processors to perform operations comprising:
obtaining, from an imaging system, first skin data associated with a user, wherein the first skin data comprises an ultraviolet (UV) image of the user's skin;
performing a correction on the first skin data, based on second skin data associated with the user, the second skin data having been collected at a time prior to obtaining the first skin data, wherein the second skin data is stored in a repository;
determining features associated with anatomy present in the first skin data;
segmenting the first skin data into a plurality of portions based on the features associated with the anatomy;
quantifying, separately for each portion of the user's skin, a plurality of skin parameters of the user's skin, wherein the at least one of the plurality of skin parameters is a bacterial load, the quantifying comprising:
applying a brightness filter that isolates portions of at least one UV image that contain fluorescence,
applying a dust filter that removes portions of the at least one UV image that contain fluorescence caused by dust particles, wherein the dust filter comprises an expectation maximization algorithm and a two-component Gaussian mixture model,
applying a loopy belief propagation algorithm that isolates portions of the at least one UV image that contain fluorescence due to bacteria, and
determining a bacterial load quantity associated with the user's skin based on an output of the loopy belief propagation algorithm;
determining, based on providing the plurality of quantified skin parameters as input features to a machine learning model, an output associated with a normal skin state of the user and a current skin state of the user; and
providing, for display on a user computing device, data indicating the output.

2. The system of claim 1, wherein the second skin data associated with the user comprises data recorded from the user's skin at multiple times prior to obtaining the first skin data.

3. The system of claim 1, wherein the second skin data and the first skin data each comprise:
at least three natural images taken in white light at three or more different angles;
at least three polarized images taken in polarized light at three or more different angles; and
at least three UV images taken in UV light at three or more different angles.

4. The system of claim 1, wherein quantifying the plurality of skin parameters further comprises quantifying:
skin pigmentation;
redness; and
skin roughness and collagen content.

5. The system of claim 1, wherein performing the correction comprises performing a color correction by:
applying a first adjustment to the first skin data based on a reference color in the second skin data;
applying a second adjustment to the first skin data by applying a histogram matching algorithm; and
applying a third adjustment to the first skin data by performing a lighting correction.

6. The system of claim 1, further comprising obtaining external data associated with the user and providing the external data as an additional input to the machine learning model.

7. The system of claim 1, wherein providing the data indicating the output comprises providing data indicating a skin care product recommendation to improve a health of the user's skin.

8. A non-transitory computer readable storage medium storing instructions that, when executed by at least one processor, cause the at least one processor to perform operations comprising:
obtaining, from an imaging system, first skin data associated with a user, wherein the first skin data comprises an ultraviolet (UV) image of the user's skin;
performing a correction on the first skin data, based on second skin data associated with the user, the second skin data having been collected at a time prior to obtaining the first skin data, wherein the second skin data is stored in a repository;
determining features associated with anatomy present in the first skin data;
segmenting the first skin data into a plurality of portions based on the features associated with the anatomy;
quantifying, separately for each portion of the user's skin, a plurality of skin parameters of the user's skin, wherein the at least one of the plurality of skin parameters is a bacterial load, the quantifying comprising:
applying a brightness filter that isolates portions of at least one UV image that contain fluorescence,
applying a dust filter that removes portions of the at least one UV image that contain fluorescence caused by dust particles, wherein the dust filter comprises an expectation maximization algorithm and a two-component Gaussian mixture model,
applying a loopy belief propagation algorithm that isolates portions of the at least one UV image that contain fluorescence due to bacteria, and
determining a bacterial load quantity associated with the user's skin based on an output of the loopy belief propagation algorithm;
determining, based on providing the plurality of quantified skin parameters as input features to a machine learning model, an output associated with a normal skin state of the user and a current skin state of the user; and
providing, for display on a user computing device, data indicating the output.

9. The medium of claim 8, wherein the second skin data associated with the user comprises data recorded from the user's skin at multiple times prior to obtaining the first skin data, and wherein the second skin data and the first skin data each comprise:
at least three natural images taken in white light at three or more different angles;
at least three polarized images taken in polarized light at three or more different angles; and
at least three UV images taken in UV light at three or more different angles.

10. The medium of claim 9, wherein quantifying the plurality of skin parameters further comprises quantifying:
skin pigmentation;
redness; and
skin roughness and collagen content.

11. The medium of claim 8, wherein performing the correction comprises performing a color correction by:
applying a first adjustment to the first skin data based on a reference color in the second skin data;
applying a second adjustment to the first skin data by applying a histogram matching algorithm; and
applying a third adjustment to the first skin data by performing a lighting correction.

12. The medium of claim 8, wherein the data indicating the output is combined with outputs of additional skin health assessments, and additional analysis is conducted based on the combination of outputs.

13. A computer-implemented skin health assessment method executed by one or more processors and comprising:
obtaining, from an imaging system, first skin data associated with a user, wherein the first skin data comprises an ultraviolet (UV) image of the user's skin;
performing a correction on the first skin data, based on second skin data associated with the user, the second skin data having been collected at a time prior to obtaining the first skin data, wherein the second skin data is stored in a repository;
determining features associated with anatomy present in the first skin data;
segmenting the first skin data into a plurality of portions based on the features associated with the anatomy;
quantifying, separately for each portion of the user's skin, a plurality of skin parameters of the user's skin, wherein the at least one of the plurality of skin parameters is a bacterial load, the quantifying comprising:
applying a brightness filter that isolates portions of at least one UV image that contain fluorescence,
applying a dust filter that removes portions of the at least one UV image that contain fluorescence caused by dust particles, wherein the dust filter comprises an expectation maximization algorithm and a two-component Gaussian mixture model,
applying a loopy belief propagation algorithm that isolates portions of the at least one UV image that contain fluorescence due to bacteria, and
determining a bacterial load quantity associated with the user's skin based on an output of the loopy belief propagation algorithm;
determining, based on providing the plurality of quantified skin parameters as input features to a machine learning model, an output associated with a normal skin state of the user and a current skin state of the user; and
providing, for display on a user computing device, data indicating the output.

14. The method of claim 13, wherein the second skin data associated with the user comprises data recorded from the user's skin at multiple times prior to obtaining the first skin data.

15. The method of claim 13, wherein quantifying the plurality of skin parameters further comprises quantifying:
skin pigmentation;
redness; and
skin roughness and collagen content.

16. The method of claim 13, wherein performing the correction comprises performing a color correction by:
applying a first adjustment to the first skin data based on a reference color in the second skin data;
applying a second adjustment to the first skin data by applying a histogram matching algorithm; and
applying a third adjustment to the first skin data by performing a lighting correction.

17. The method of claim 13, further comprising obtaining external data associated with the user and providing the external data as an additional input to the machine learning model.

18. The method of claim 13, wherein the data indicating the output is combined with outputs of additional skin health assessments, and additional analysis is conducted based on the combination of outputs.

* * * * *